United States Patent [19]

Noiles

[11] 3,996,625
[45] Dec. 14, 1976

[54] ARTIFICIAL HIP JOINT WITH NOVEL STEM

[75] Inventor: Douglas G. Noiles, New Canaan, Conn.

[73] Assignee: United States Surgical Corporation, New York, N.Y.

[22] Filed: Feb. 28, 1975

[21] Appl. No.: 554,126

[52] U.S. Cl. ........................ 3/1.912; 3/1.91; 128/92 C; 128/92 CA
[51] Int. Cl.² ........................................... A61F 1/24
[58] Field of Search ................... 3/1, 1.9–1.913; 128/92 C, 92 CA, 92 BC

[56] References Cited

UNITED STATES PATENTS

| | | | |
|---|---|---|---|
| 2,490,364 | 12/1949 | Livingston | 128/92 BA |
| 2,696,817 | 12/1954 | Prevo | 128/92 C |
| 2,719,522 | 10/1955 | Hudack | 128/92 CA |
| 3,067,740 | 12/1962 | Haboush | 128/92 CA |
| 3,579,831 | 5/1971 | Stevens et al. | 128/92 C |
| 3,805,302 | 4/1974 | Mathys | 3/1.91 |
| 3,846,846 | 11/1974 | Fisher | 128/92 BB |
| 3,848,272 | 11/1974 | Noiles | 128/92 CA |

FOREIGN PATENTS OR APPLICATIONS

| | | | |
|---|---|---|---|
| 493,526 | 2/1950 | Belgium | 128/92 CA |
| 471,394 | 5/1952 | Italy | 128/92 CA |

*Primary Examiner*—Ronald L. Frinks
*Attorney, Agent, or Firm*—Fleit & Jacobson

[57] ABSTRACT

An artificial hip joint including an acetabulum prosthesis for the cotyloid cavity defining a socket and having a plurality of outwardly extending blades for engaging the prepared wall of the cavity together with a prosthesis of the head of the femur movably interconnected with the acetabulum prosthesis and which includes a pin arranged to be driven into the bone-marrow channel of the femur, a neck connected integrally to the pin and a hip ball secured to the neck and movably disposed within the socket, the pin including a tapered upper portion and a lower portion provided with a plurality of longitudinally extending flutes to prevent rotation of the pin and a pair of rows of slots or holes arranged in diametrically opposed relationship on both the pin upper and lower portions for promoting bone ingrowth.

7 Claims, 5 Drawing Figures

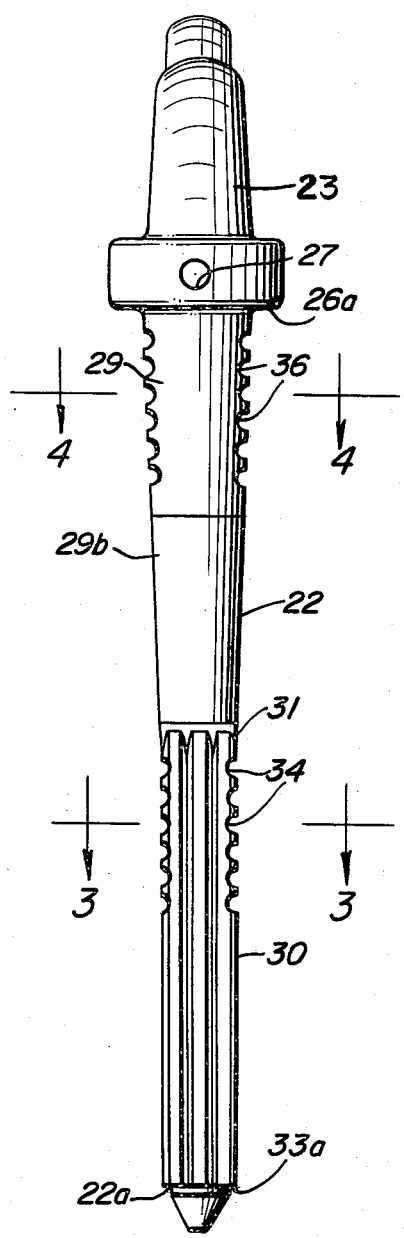
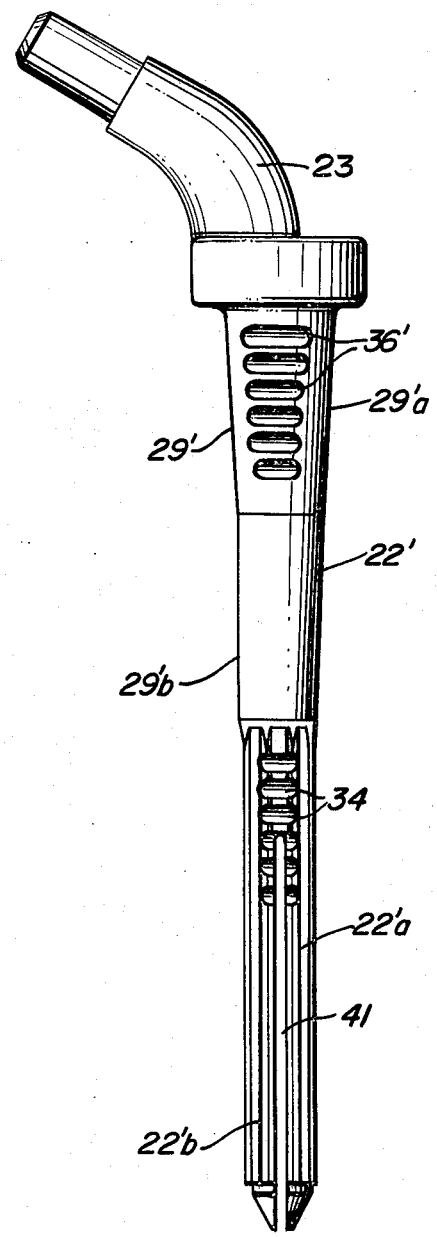
Fig. 2
Fig. 5

ARTIFICIAL HIP JOINT WITH NOVEL STEM

BACKGROUND OF THE INVENTION

The present invention relates to artificial joints and more particularly to an artificial hip joint.

The replacement of damaged or diseased portions of the human body is commonly practiced today in the field of medicine, and such replacement techniques include bone replacement in which the methods and techniques employed permit the replacement of such complicated, articulated bone structures as body joints of which knee and hip joints are representative. Not only have such bone replacement techniques reached a high level of sophistication, but many structures and materials have been developed which permit the artificial joint to perform in virtually the same manner as that of the original joint over indefinite periods of time with a minimum of discomfort. An example of such an artificial joint which is being used successfully today is shown in U.S. Pat. No. 3,848,272, entitled Artificial Hip Joint, issued to Douglas G. Noiles on Nov. 19, 1974 and in U.S. Pat. No. 3,820,167, entitled Artificial Hip Joint, issued to Konstantine M. Savish on June 28, 1974.

The artificial hip joint of the aforementioned patents produces outstanding results such as ease of implantation, the absence of corrosion by the body environment and the like. However, since such artificial hip joints are intended to be permanently installed in the body, hopefully without repair or replacement for the life of the patient, it is extremely important that such an artificial joint be secured to the existing supporting bone in the body in an immovable position and remain so indefinitely. As is well known, a hip joint is a portion of the body which is subjected to considerable stress and wear, and therefore unless the artificial joint is securely fixed, relative movement between the joint and the supporting bone, however slight, can occur causing partial immobilization of the joint with a concomitant gradual increase of painful sensations.

If such partial immobilization and pain persists, the patient has little recourse but to undergo additional corrective surgery.

Accordingly, the primary object of this invention is to provide an artificial hip joint which will remain permanently fixed in the body with the elimination of pain to the patient and with full mobility at all times.

Another object of this invention is to provide an artificial hip joint which is securely and permanently attached to the supporting bone structure so as to eliminate the need for eventual replacement due to loosening.

A further object of this invention is to provide an artificial hip joint which promotes the growth of bone for holding the joint permanently in position and for providing support during functional loading of the joint.

A still further object of this invention is to provide an artificial hip joint which avoids the splitting of the bone in a hard and/or brittle femur during installation of the joint.

This invention further contemplates the provision of an artificial hip joint which may be installed in the body using well known surgical techniques, which is adaptable to a wide variety of sizes for both humans and animals alike, which induces bone growth in specific areas to eliminate joint movement and for spreading the vertical loading on the joint and which permits implantation of the joint without damage to the supporting bone.

These and other objects of the invention, as well as many of the attendant advantages thereof, will become more readily apparent when reference is made to the following description taken in conjunction with the accompanying drawings.

SUMMARY OF THE INVENTION

To achieve these and other objects, the present invention provides an artificial hip joint including an acetabulum prosthesis of the cotyloid cavity defining a socket and having a plurality of blades extending outwardly away from the socket for engaging the prepared wall of the cavity and a prosthesis of the head of the femur movably interconnected with the acetabulum prosthesis including an elongated pin arranged to be driven into the bone-marrow channel of the femur, a neck integrally connected at one end to the upper end of the pin and a hip ball secured to the other end of the neck and movably disposed within the socket. The pin includes an upper or proximal portion tapered away from the joint and a distal portion extending from the proximal portion to the pin distal end, the lower or distal portion of the pin having an outer diameter corresponding to the smallest diameter of the tapered portion. The pin lower or distal portion is provided with a plurality of circumferentially spaced, longitudinally extending grooves defining upstanding flutes therebetween and at least one row of longitudinally spaced recesses are provided on the outer surface of the pin lower or distal portion. Additionally, at least one row of longitudinally spaced slots or holes are provided on the outer surface of the pin upper or proximal portion. As used herein, "proximal" and "distal" are relative to the joint end of the pin.

It is to be understood, of course, that both the foregoing general description and the following detailed description are explanatory only and are not restrictive of the invention.

The accompanying drawings, which are incorporated in and constitute part of the specification, illustrate the preferred embodiments of the invention, and together with the description, serve to explain the principles of the invention.

BRIEF DESCRIPTION OF THE DRAWINGS

FIG. 2 is a side elevation view of the artificial hip joint in FIG. 1;

FIG. 5 is a partial view of a portion of the invention showing an alternate construction.

DESCRIPTION OF THE PREFERRED EMBODIMENTS

Figure 1:
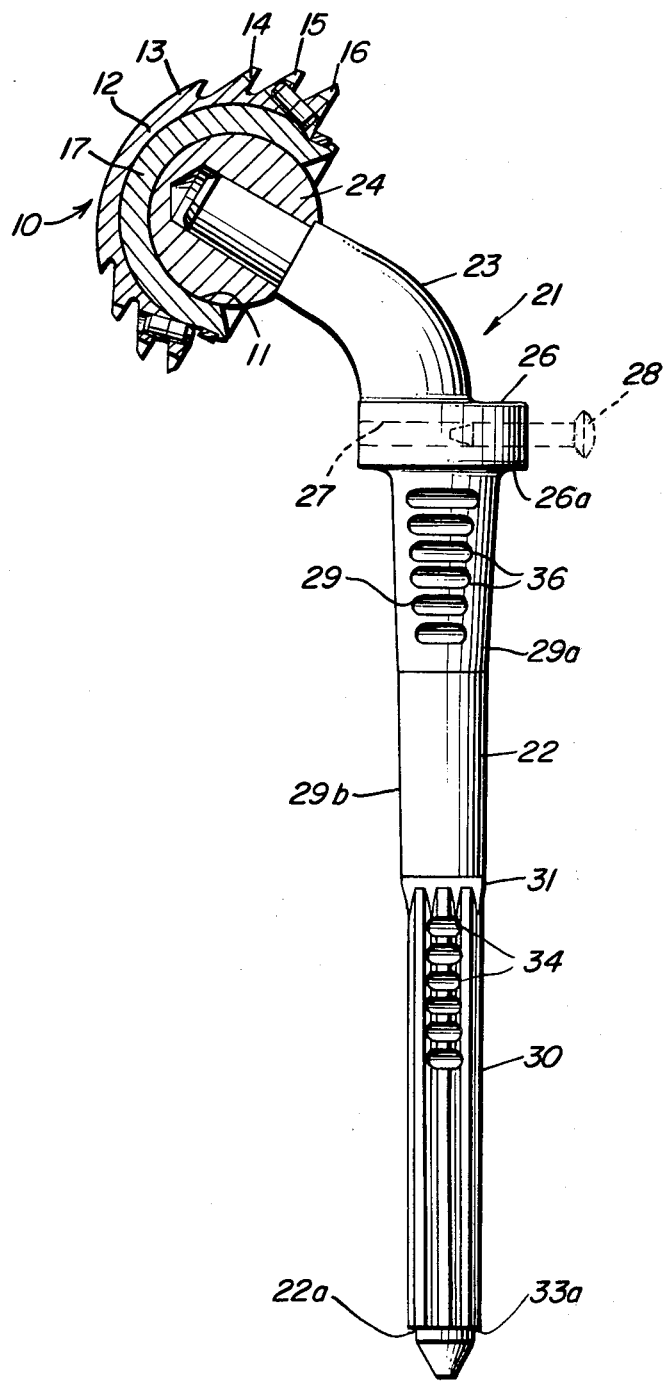
FIG. 1 is a plan view of the artificial hip joint of the invention.

With reference now to the drawings, wherein like reference characters designate like or corresponding parts throughout the several views, there is shown in FIG. 1 a machined acetabulum prosthesis 10 of the cotyloid cavity defining a socket 11 and including an acetabular component 12. A plurality of blades 13, 14, 15 and 16 extend outwardly away from the socket 11 for engaging the prepared wall (not shown) of the cotyloid cavity. An insert 17 suitably shaped and formed of a suitable material such as ultra high molecular weight polyethylene or the like is disposed within the acetabular component 12, the inner surface of which defines the socket 11 and provides a bearing surface as will be explained hereinafter.

A machined prosthesis 21 of the femur is movably interconnected with the acetabulum prosthesis 10 and includes a stem or elongated pin 22 arranged to be driven into the bone-marrow channel of the femur (not shown), a neck 23 integrally connected at one end to the pin 22 and a hip ball 24 positioned on the neck and movably located within the socket 11 against the bearing surface of the insert 17 as shown.

The prosthesis 21 of the femur also preferably includes an enlarged shoulder 26 formed integrally with and positioned between the pin 22 and the neck 23. The shoulder 26 has a lower surface 26a which rests on the upper portion of the severed femur when the artificial hip joint is installed. The shoulder 26 is also provided with a transverse hole 27 through which a rod 28, extending through a hole drilled in the greater trochanter (not shown), is to be driven, to hold the greater trochanter in the proper position after the artificial joint has been implanted.

As specifically illustrative of the invention, the pin 22 includes an upper portion 29 tapered inwardly downward as shown in FIG. 1 and a lower portion 30 extending from the upper portion to the pin lower end 22a. The intersection between the pin upper and lower portions 29, 30 is designated in FIG. 1 by the number 31, and the pin lower portion 30 has an outer diameter corresponding to the outer diameter of the lower end of the pin upper portion 29 at the intersection 31.

Preferably, the pin tapered upper portion 29 comprises an upper and lower section 29a and 29b respectively, and section 29a having a taper of about 3° and section 29b having a taper of about 1°. As is well known, the pin upper portion 29 is disposed within cancellous or spongy bone which readily accepts an impacting press fit.

Figure 3:
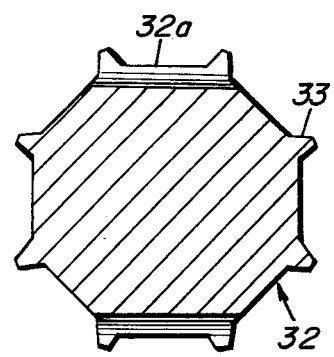
FIG. 3 is an enlarged sectional view taken substantially along lines 3—3 of FIG. 2 in the direction of the arrows.
Figure 4:
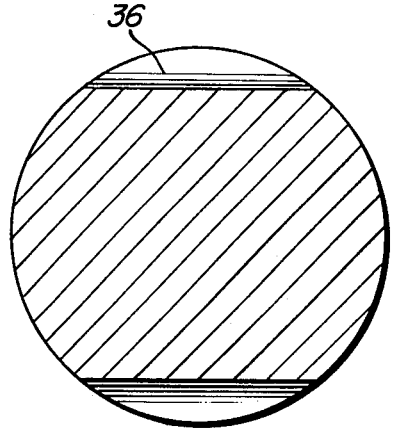
FIG. 4 is an enlarged sectional view taken substantially along lines 4—4 of FIG. 2 in the direction of the arrows.

As shown best in FIG. 3, the pin lower portion 30 is provided with a plurality of circumferentially spaced, longitudinally extending grooves 32 having an outer surface 32a defining therebetween upstanding flutes 33. In the preferred embodiment, eight of such grooves and flutes are provided and the apex of the flutes 33 is provided with a cutting edge 33a for biting into the inner wall of the bone-marrow channel as the pin is being driven in.

The pin lower portion 30 is also provided with at least one row of longitudinally spaced, transversely extending slots 34 and, in the preferred embodiment, a pair of such rows of slots 34 are provided on the lower portion disposed in diametrically opposed relationship as shown best in FIG. 2. Each of the rows of slots 34 may be located in any selected longitudinal position on the pin lower portion 30 and, in the preferred embodiment, six of such slots 34 are provided in each row although it should be understood that more of such slots 34 may be provided to form macro-porosites in the pin 22 for promoting bone ingrowth as will be explained hereinafter. As shown best in FIG. 3, the slots 34 preferably extend through one pair of adjacent flutes 33 below the outer surface 32a of the grooves 32.

The pin 22 is also provided with at least one row of longitudinally spaced, transversely extending slots 36 in the outer surface of the pin upper portion 29. In the preferred embodiment, a pair of rows of slots 36 are provided on the pin upper portion 29 arranged in diametrically opposed relationship, each of said rows containing at least six such slots 36. However, it should be understood that any selected number of slots 36 may be provided to form macro-porosites for promoting bone ingrowth as discussed above with reference to the slots 34. Preferably, each of the rows of slots 34, 36 are in longitudinally aligned relationship although such an arrangement is not critical to the objectives of the invention. However, it will be noted that the pair of rows of slots 36 positioned adjacent the shoulder 26 is located on the neutral axis of stress in the pin upper portion 29. Thus, the slots are located in the area where stresses of functional loading of the pin are at a minimum. Accordingly, this location of slots 36 minimizes weakening of the pin 22.

When the artificial hip joint of the invention is to be installed, the body bone structure is prepared in conventional surgical manner. Thus, the cotyloid cavity is suitably prepared and the femur is reamed to a diameter approximately 1 mm less than the outer diamter of the pin. The pin 22 is driven into the bone-marrow channel so that the flutes bite or cut into the bone wall of the reamed femur channel embedding the flutes therein so as to provide firm resistance to rotation of the pin within the bone.

The proximal femur has also been prepared by reaming a hole to a diameter approximately 1 mm less than the outer diameter of the pin upper portion 29. Thus, when the pin 22 is driven into the bone, a tight, impacted press fit is secured between the pin 22 and the bone so as to stimulate regeneration of bone. After the prosthesis of the femur 21 has been implanted, the acetabular prosthesis 10 is reduced and fixed in the cotyloid cavity.

As a result of the plurality of slots 34, 36 in the pin 22 forming macro-porosites, bone subsequently will grow into these slots, it having been established that bone will grow into pores of a size greater than 150 microns. Not only does such new bone resist rotation of the pin 22 but the new bone ingrowth will provide vertical support for the prosthesis by spreading the vertical loading of the prosthesis over a greater amount of bone area than that which would normally exist without the slots. Thus, both slots 34, 36 perform dual functions in resisting pin rotation and in providing axial stress support.

FIG. 5 shows a modification of the artificial hip joint of the invention wherein the pin, designated by the numeral 22', is provided with a slot 41 extending longitudinally through the apex of the pin from a point near the upper end of the pin lower portion 30 the end of the pin. The slot 41 divides the pin 22' into a pair of flexible sections 22'a, 22'b so that when the pin 22' is inserted into the bone-marrow channel, the sections 22'a, 22'b may move inwardly together thereby relieving the force exerted on the inner wall of the bone-marrow channel. This is desirable since the pin lower portion 30 contacts the cortical or hard bone of the femur in the implanted position of the pin. such cortical bone resists the press fit and cutting by the flutes 33. Thus, the degree of resistance to the insertion of the pin throughout the pin lower portion 30 depends on the hardness of the bone.

In addition, the provision of the sections 22'a, 22'b formed by the slot 41 permit the surgeon to deform the sections 22'a, 22'b outwardly to fit the medullary canal of a patient's femur which may be large relative to the rest of the bone anatomical geometry.

There has above been described specific embodiments of the present invention. It should be noted, however, that the above embodiments were given for illustrative purposes only and that many alterations and modifications can be practiced by those skilled in the art without departing from the spirit or scope of the present invention. For example, the transversely extending slots 34, 36 can be replaced by a geometrically similar pattern formed by a plurality of holes. Accordingly, it is the intent that the present invention not be limited to the embodiments illustrated, but only as defined in the appended claims.

I claim:

1. An artificial hip joint comprising an acetabulum prosthesis of the cotyloid cavity defining a socket and a femoral prosthesis including a pin adapted to be driven into the bone-marrow channel of the femur, a neck integrally connected to the pin and a hip ball secured to the neck and movably interconnected with said acetabulum prosthesis, said pin having a proximal portion tapered away from the joint and a distal portion having a plurality of circumferentially spaced longitudinal flutes, said flutes having a longitudinally extending cutting edge adpated to cut into the inner wall of the bone-marrow channel, said pin further having a plurality of longitudinally spaced recesses located on the surface of said pin, said recesses comprising slots or a plurality of holes extending transversely of said pin, said recesses being only located on the surface of the pin at points which are intersected by a plane which is perpendicular to an imaginary plane passing through the centers of the hip ball, neck and pin of the femoral prosthesis, said pin further having a longitudinal slot extending away from the distal end toward the joint, said slot extending completely through the distal portion of the pin and dividing the distal portion into a pair of flexible sections so that the sections may move inwardly and outwardly relative to each other.

2. An artificial hip joint in accordance with claim 1, wherein the distal portion of the pin is of smaller diameter than the diamter of the proximal portion of the pin.

3. an artificial hip joint in accordance with claim 1, wherein at least six of said flutes are provided on said distal portion.

4. An artificial hip joint in accordance with claim 1, wherein said flutes are approximately 1 millimeter in height.

5. An artificial hip joint in accordance with claim 1, wherein two rows of said recesses are provided in diametrically opposed relationship on said pin.

6. An artificial hip joint in accordance with claim 5, wherein each of said two rows of said recesses include at least six of said recesses.

7. An artificial hip joint in accordance with claim 1, wherein said tapered portion includes two sections having different angles of taper, the angle of taper of the section proximal to the joint being greater than the angle of taper of the section distal to the joint.

* * * * *